(12) United States Patent
Filippi et al.

(10) Patent No.: US 11,320,063 B2
(45) Date of Patent: May 3, 2022

(54) VISUAL POSITIONING INDICATOR ASSEMBLY FOR LIMIT SWITCH BOXES

(71) Applicant: EISENBAU S.R.L., Cusago (IT)

(72) Inventors: Alessandro Filippi, Montichiari (IT); Lorenzo Baccolo, Lonato del Garda (IT)

(73) Assignee: EISENBAU S.R.L., Cusago (IT)

( * ) Notice: Subject to any disclaimer, the term of this patent is extended or adjusted under 35 U.S.C. 154(b) by 996 days.

(21) Appl. No.: 16/061,472

(22) PCT Filed: Dec. 20, 2016

(86) PCT No.: PCT/IB2016/057836
§ 371 (c)(1),
(2) Date: Jun. 12, 2018

(87) PCT Pub. No.: WO2017/109704
PCT Pub. Date: Jun. 29, 2017

(65) Prior Publication Data
US 2020/0232580 A1    Jul. 23, 2020

(30) Foreign Application Priority Data
Dec. 24, 2015   (IT) .................. 102015000087723

(51) Int. Cl.
*F16K 37/00* (2006.01)
*A61N 1/36* (2006.01)
*F16K 31/08* (2006.01)

(52) U.S. Cl.
CPC ...... *F16K 37/0008* (2013.01); *F16K 37/0041* (2013.01); *A61N 1/36135* (2013.01);
(Continued)

(58) Field of Classification Search
CPC ............. F16K 37/0008; F16K 37/0041; F16K 31/088; F16K 37/0033; F16K 37/0058; A61N 1/36135
See application file for complete search history.

(56) References Cited

U.S. PATENT DOCUMENTS 5,178,187 A * 1/1993 Raymond, Jr. ..... F16K 37/0058
116/277
5,223,822 A * 6/1993 Stommes ............ F16K 37/0008
116/277
(Continued)

FOREIGN PATENT DOCUMENTS

EP           2573439           3/2013

OTHER PUBLICATIONS

International Search Report and Written Opinion for International Application No. PCT/IB2016/057836 (Mar. 21, 2017). (10 Pages).

*Primary Examiner* — Angelisa L. Hicks
(74) *Attorney, Agent, or Firm* — Lucas & Mercanti, LLP

(57) ABSTRACT

A visual position indicator assembly for limit switch boxes is provided. The indicator assembly has an indicator element configured to be fitted to a shaft of a driving assembly of a limit switch box, and the indicator element has a plurality of adjacent sectors featuring different colors and/or writings. The visual position indicator assembly further has a first mask and a second mask that are both provided with through apertures having the same size and arrangement and that are fitted coaxially to each other. One between the first mask and the second mask is rotatable with respect to the other one. Thanks to this configuration, it is possible to vary the angular width of the through apertures in order to adapt it to the real angular stroke of the indicator element.

7 Claims, 5 Drawing Sheets

(52) U.S. Cl.
CPC ........ *F16K 31/088* (2013.01); *F16K 37/0033* (2013.01); *F16K 37/0058* (2013.01)

(56) References Cited

U.S. PATENT DOCUMENTS

| | | | |
|---|---|---|---|
| 6,820,647 B1 | 11/2004 | Grecco | |
| 7,819,133 B2 * | 10/2010 | Minervini | F16K 37/0033 137/556 |
| 8,375,883 B2 * | 2/2013 | Soldo | H01H 9/02 116/277 |
| 2011/0290332 A1 * | 12/2011 | Soldo | F16K 37/0033 137/15.01 |
| 2015/0204457 A1 | 7/2015 | Jordan | |

* cited by examiner

VISUAL POSITIONING INDICATOR ASSEMBLY FOR LIMIT SWITCH BOXES

CROSS-REFERENCE TO RELATED APPLICATIONS

This application is a 371 of PCT/IB2016/057836, filed Dec. 20, 2016, which claims the benefit of Italian Patent Application No. 102015000087723, filed Dec. 24, 2015.

Field of the Invention

The present invention generally relates to devices for monitoring the position of manually or automatically operated valves and actuators, such as those used in chemical and petrochemical plants. More particularly, the invention concerns a visual position indicator assembly for limit switch boxes.

Background of the Invention

Known control devices provided with limit switches, also called "Limit Switch Boxes", are used to control the position of valves and actuators in chemical and petrochemical plants. Such devices comprise an electric circuit on which one or more limit switches are mounted, as well as a driving assembly comprising a shaft connectable to a valve or to an actuator through a suitable coupling. The driving assembly further comprises one or more cams keyed on the shaft and configured to interact with respective limit switches so as to allow or inhibit operation of the valve or actuator.

The cams can control the respective limit switches directly when the limit switches are configured as push buttons, or indirectly by way of a ferromagnetic element or a magnet associated therewith, when the limit switches are configured as proximity sensors.

The driving assembly and the electrical circuit are generally accommodated in a container that protects them from atmospheric agents and that can be possibly configured to resist fire and/or explosions.

The container is provided with a position indicator assembly associated with the shaft, which allows operators to visually and quickly obtain information about the position of a valve or an actuator, corresponding to the position detected by the limit switches.

Known visual position indicator assemblies include an indicator element configured to be fitted on the shaft of the driving assembly and a cap-shaped mask configured to be fixed, typically by way of screws, on the container inside which the driving assembly is housed. The cap-shaped mask is fixed at an opening from which the indicator element partially protrudes. The surface of the indicator element is provided with a plurality of adjacent sectors alternately bearing writings such as "OPEN" and "CLOSED" and the like, and/or alternating colors, for example red and green. The mask includes a plurality of through apertures whose size substantially corresponds to the size of the sectors of the indicator element.

The overall configuration of a visual position indicator assembly is such that sectors of the indicator element having any one of the two colors, and/or any one of the two writings are visible through the apertures of the mask depending on the relative position the indicator element has relative to the mask as a consequence of the rotation of the shaft of the driving assembly. The writing "OPEN" and/or the green color may for example indicate an operating or open condition of a valve or an actuator, whereas the writing "CLOSED" and/or the red color may indicate a rest condition of the valve or the actuator.

Known driving assemblies used in limit switch boxes are typically provided with means for adjusting the angular position of the cams, which on the one hand allows to achieve a good level of standardization, and on the other makes it possible to easily adapt their positions to the arrangement of the respective switches and/or proximity sensors arranged on the electric circuit in order to control a specific valve or actuator. The position of these switches and/or proximity sensors in fact derives from the stroke of the respective valves or actuators.

Control devices having limit switch boxes do not however allow to adjust the angular positions of the components of the visual position indicator assembly so as to adapt them to the specific configuration of a valve or actuator. In fact, the indicator element is typically keyed on the shaft of the driving assembly at a fixed angular position, e.g. by way of a prismatic coupling, and the mask is fixed on the container of a control device for example by way of screws.

It will thus be appreciated that if a same control device is used with a plurality of valves and/or actuators that determine different angular strokes of the indicator element, the related visual position indicator assembly cannot allow to properly visualize the operation conditions of all valves and/or actuators. It typically happens that the indicator assembly a pair of adjacent sectors of the indicator element with the respective different writings and/or colors are shown through the mask apertures. This condition may be tolerated when one of the two operating information prevails on the other one, but is totally unacceptable when the portions of adjacent sectors visible through an aperture of the mask have the same size, because a user cannot know the real operation condition of the valve or actuator connected to the control device.

A possible solution to this problem is to use for each valve or actuator connected to a limit switch box a specific shaft of the driving assembly, and/or a specific indicator element, which results in a low level of standardization of the components and results in high manufacturing and installation costs.

SUMMARY OF THE INVENTION

The object of the present invention is therefore to provide a visual position indicator assembly for limit switch boxes that is free from said drawbacks. Said object is achieved with an indicator assembly whose main features are specified in the first claim, while other features are specified in the remaining claims.

An idea of solution underlying the invention is to make a visual position indicator assembly comprising an indicator element having adjacent sectors with colors and/or writings indicating an operation condition, as well as a first mask and a second mask both of which have through apertures with the same size and arrangement, wherein the masks are fitted coaxially into one another and wherein one mask is rotatable relative to the other mask. Thanks to this configuration it is possible to vary the angular size of the through apertures so as to adapt it to the real angular stroke of the indicator element, as actually determined by the specific valve or actuator connected to the shaft of the driving assembly of the control device.

The main advantage offered by the invention is therefore to allow to use a same visual position indicator assembly, and hence a same limit switch box, with more types of valves and actuators having different operation strokes, thus being able to display to a user visual indications of their operating conditions that are always precise and reliable.

It is therefore possible to standardize the components of the indicator assembly, which allows to reduce its manufacturing costs.

The rotatable mask is preferably the inner one, while the external one is fixed on the container of the control device. The relative position between the two masks is adjusted when mounting the indicator assembly. The complete fastening of the outer mask e.g. by way of screws on the container of the control device determines a compression of the masks on each other, thereby and locking their relative position by friction.

The indicator assembly further comprises a protective cap made of a transparent material adapted to prevent water from entering the control device.

According to a preferred embodiment of the invention, the protective cap is arranged between the first mask and the second mask and is integral with the second mask, i.e. the inner one, thus reducing the number of parts of the indicator assembly to be mounted and providing a gripping surface for maneuvering the second mask when mounting the indicator assembly, which facilitates positioning of the second mask relative to the first mask.

BRIEF DESCRIPTION OF THE DRAWINGS

Further advantages and features of the visual position indicator assembly according to the present invention will become clear to those skilled in the art from the following detailed and non-limiting description of embodiments thereof with reference to the attached drawings, wherein.

DETAILED DESCRIPTION OF THE INVENTION

Referring to FIGS. 1 to 5, a visual position indicator assembly according to the invention for limit switch boxes is generally indicated by reference number 100 and is shown in a triaxial reference system wherein an X axis and an Y axis perpendicular to each other represent a horizontal plane of the indicator assembly 100, while a Z axis, perpendicular to the X and Y axes, represents a direction along which the indicator assembly stretches out vertically.

Figure 1:
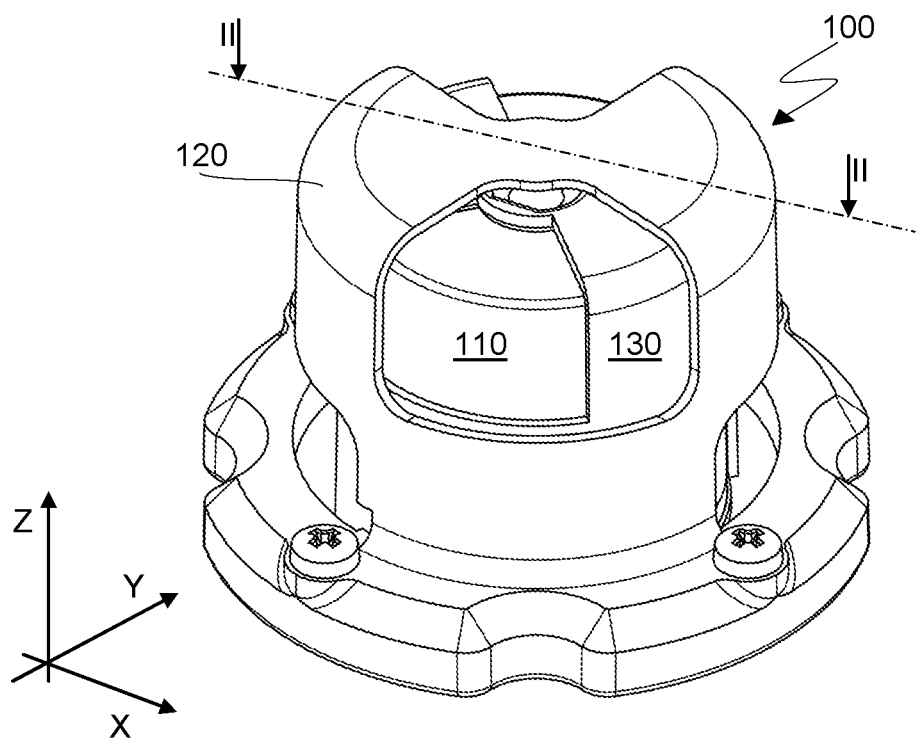
FIG. 1 is a top perspective view showing a visual position indicator assembly according to the invention for limit switch boxes.
Figure 2:
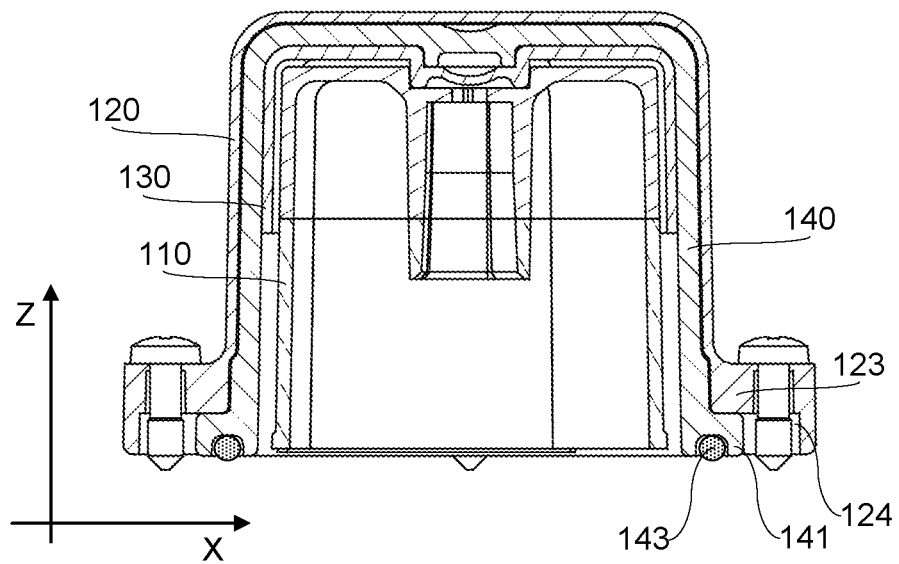
FIG. 2 is a longitudinal sectional view of the indicator assembly according to the invention taken along a plane passing through line II-II of FIG. 1.
Figure 3:
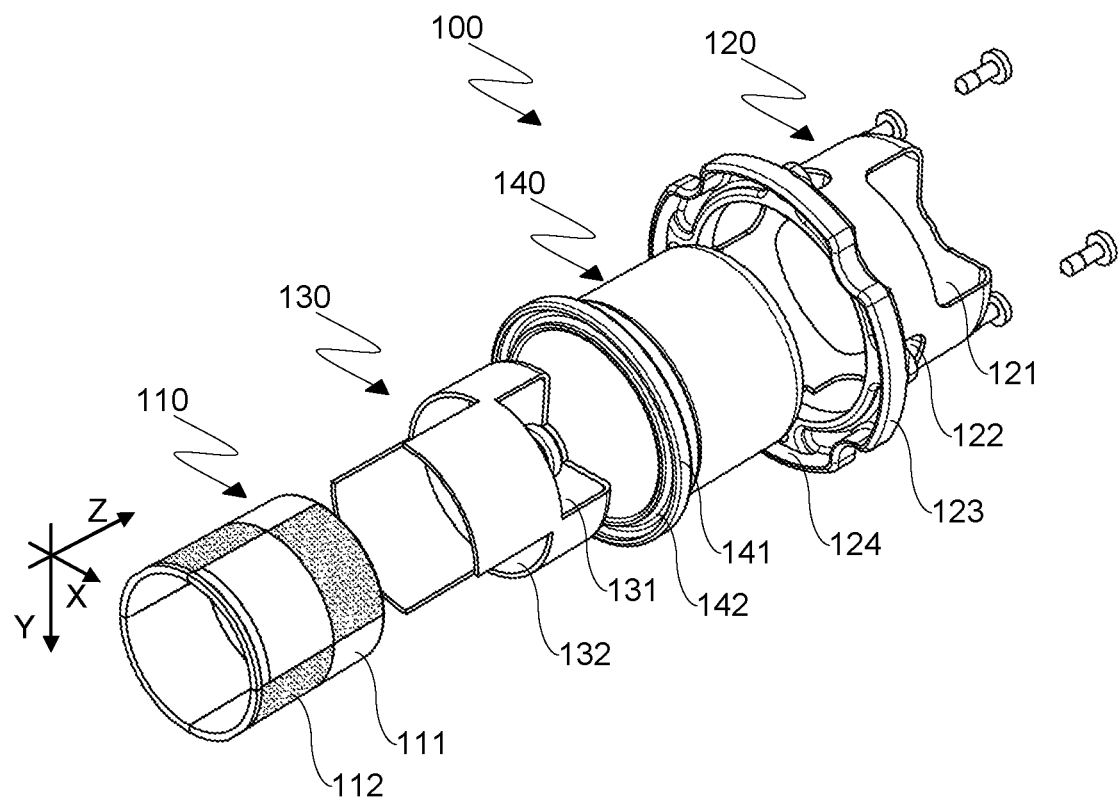
FIG. 3 is an exploded perspective view from below of the indicator assembly according to the invention.
Figure 4:
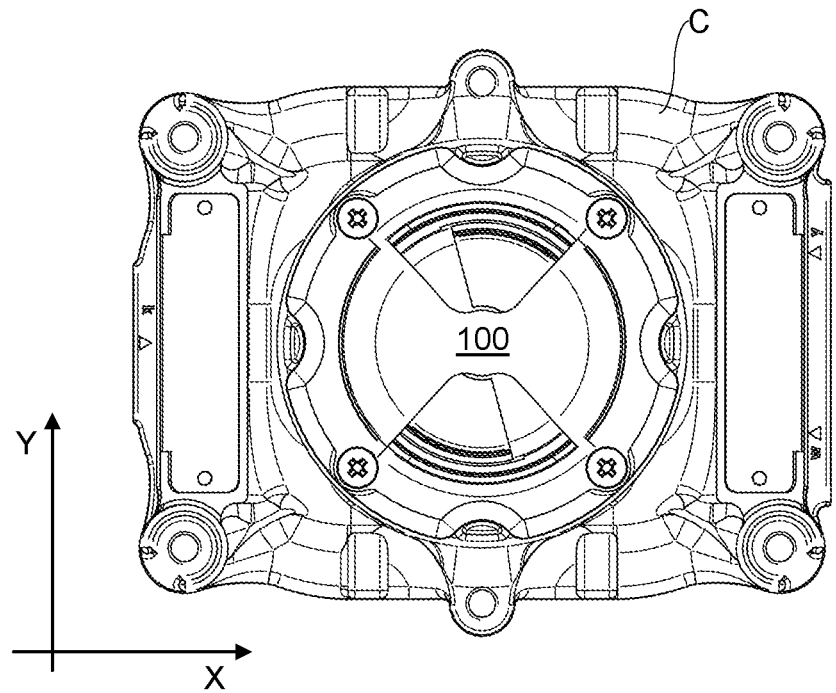
FIGS. 4 and 5 are a top plan view and a partial, longitudinal sectional view, respectively, of a limit switch box on which the indicator assembly according to the invention is mounted.
Figure 5:
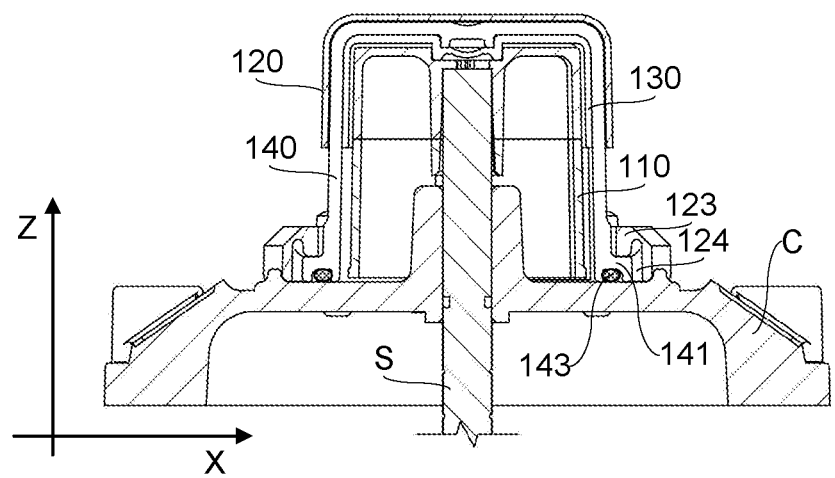

The indicator assembly 100 includes an indicator element 110, for example having cylindrical shape, configured to be connected to a shaft S of a driving assembly of a limit switch box. FIGS. 4 and 5 show a container C of the limit switch box and the end of the shaft S of the driving assembly on which the indicator element 110 is fitted.

To this aim the indicator element 110 may e.g. comprise a seat having a prismatic shape configured to be coupled with an end of the shaft S having a corresponding shape.

The side surface and the top of the indicator element 110 are provided with a plurality of sectors 111, 112 adjacent to one another and alternately featuring a first color and a second color that are different from each other, for example red and green. In the illustrated embodiment the sectors 111, 112 having different colors are respectively schematically shown with different patterns. In addition or alternatively, the sectors 111, 112 may have alternate writings such as "OPEN" and "CLOSED" and the like, which describe an operation condition.

The indicator assembly 100 further comprises a first, cap-shaped mask 120, for example cylindrical shaped, configured to be fixed on a container of the limit switch box inside which the driving assembly is housed. It is known that the mask 120 is intended to be fixed coaxially to an opening of the container C from which the indicator element 110 partially protrudes.

The first mask 120 includes a plurality of through apertures 121, 122 formed at different heights in the vertical direction Z in its lateral surface, as well as on its top, whose size and angular width substantially correspond to the size and angular width of the sectors 111, 112 of the indicator element 110. In an assembled configuration of the indicator assembly, the through apertures allow to display the sectors of the indicator element, and hence the operation or rest condition of a valve or of an actuator connected to the driving assembly.

The first mask 120 may further include a flange 123 provided with a plurality of mounting holes suitable to allow to assemble it on the container of a limit switch box typically by way of screws.

In the illustrated embodiment, the indicator element 110 and the first mask 120 comprise sectors and corresponding apertures e.g. having an angular width of 90° and a height that is substantially half the height of the indicator element 110 and of the mask 120. Furthermore, the apertures 122 of the first mask 120 formed proximate the flange 123 have an angular offset, e.g. 90°, relative to the apertures 121 formed in an upper half of the mask 120, which also extend on its top. It will be appreciated that these are not limiting features of the invention, because the sectors and the apertures might have different heights and angular widths, e.g. 180°.

According to the invention, the indicator assembly 100 further comprises a second mask 130, also having the shape of a cylindrical cap. The second mask 130 is coaxially fitted on the first mask 120 in an assembled configuration of the indicator assembly 100.

Similarly to the first mask 120, the second mask 130 includes a plurality of through apertures 131, 132 formed in its lateral surface and on the top. The second mask 130 may further comprise a flange (not shown) intended to be housed in a seat 124 formed in the flange 123 of the first mask 120.

The through apertures 131, 132 formed in the second mask 130 have a size and an angular width that substantially correspond to the size and angular width of the apertures formed in the first mask 120.

Figure 6:
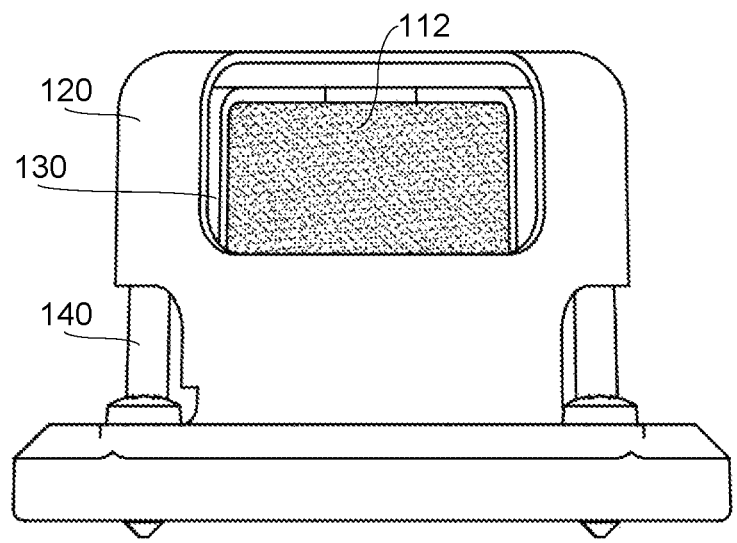
FIGS. 6 and 7 are a side view and a top plan view, respectively, showing an operating configuration of the indicator assembly of FIG. 1, wherein the apertures of the two masks are fully aligned.
Figure 7:
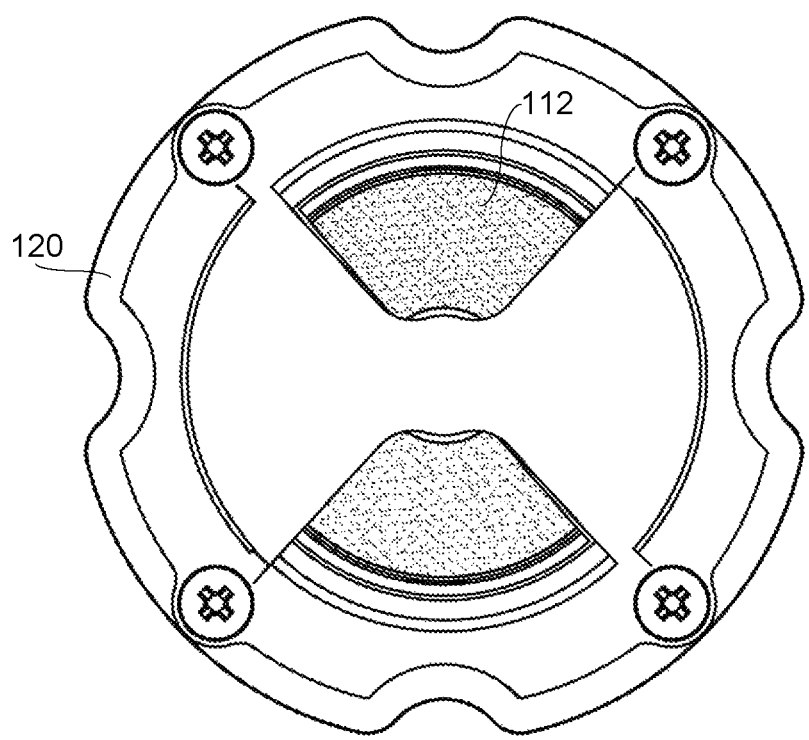
Figure 8:
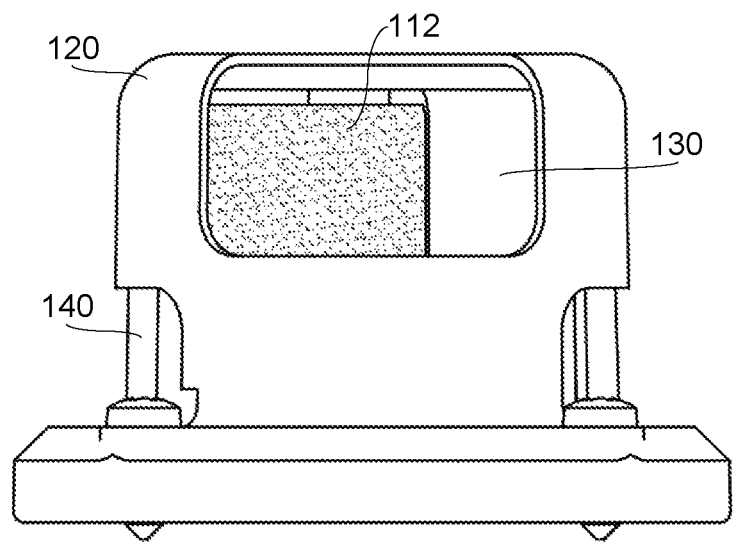
FIGS. 8 and 9 are a side view and a top plan view, respectively, showing a different operating configuration of the indicator assembly of FIG. 1, wherein the apertures of the two masks have an angular offset.
Figure 9:
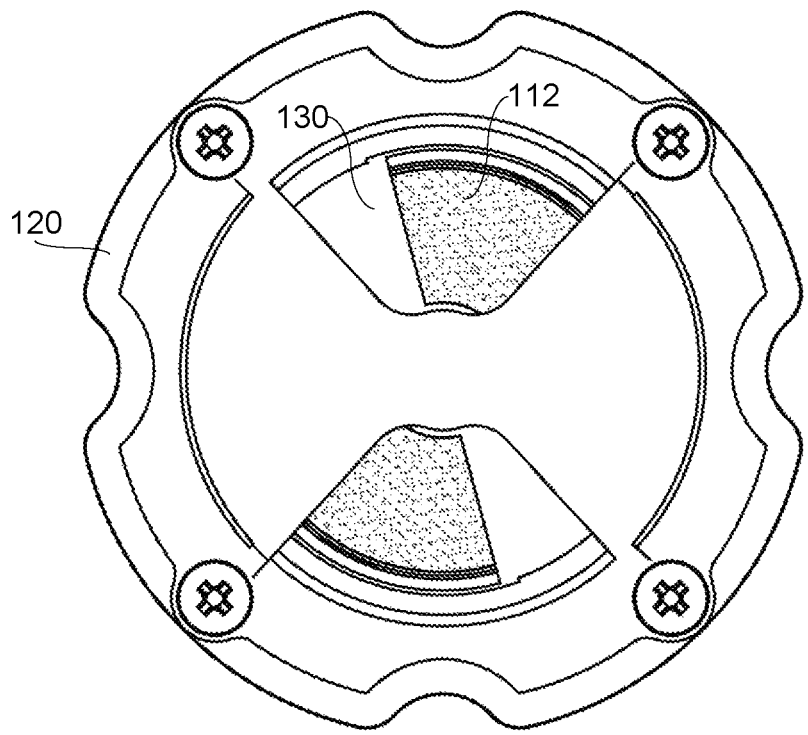

The second mask 130 is rotatably housed in the first mask 120, so that it is possible to arranged a mask relative to the other one in such a way that their through apertures 121, 122, 131, 132 are fully superimposed as shown in FIGS. 6 and 7, or have an angular offset so as to define apertures having a smaller angular size, corresponding to the actual angular stroke of the indicator element 110. It is known that the stroke of the indicator element 110 will be determined by the rotation of the driving assembly shaft on which it is intended to be keyed. An example of an offset configuration is shown in FIGS. 8 and 9, wherein the offset angle is approximately 30° and the resulting through apertures have an angular width of 60°.

Adjustment of the relative angular position between the first mask 120 and the second mask 130 is carried out during assembly. Once known the actual angular stroke of the indicator element 110, as determined by the actuator or valve connected to the shaft of the driving assembly, the angular position of the second mask 130 is fixed by rotating it axially relative to the first mask 120, whose position is instead established by the mounting holes of the container of the limit switch box.

It will be appreciated that it is not essential in the invention that the first mask is fixed and the second is rotatably assembled. In fact, in an entirely equivalent way it is possible to configure the second mask to be fixed on the container of the limit switch box and rotate the first mask relative to the second mask. In this case locking of the first mask at the desired angular position may be carried out by e.g. gluing or ultrasonic welding.

However, the configuration of the indicator assembly 100 described above and shown in the drawings is preferred, because it is cheaper and can be disassembled for maintenance and possible repairs.

The indicator assembly 100 also comprises in known manner a protective cover 140 made of a transparent material. The cover 140 is configured to be mounted on the container of the limit switch box in order to make it water resistant.

The protective cap 140 may for example be mounted on the first mask 120 as in the known indicator assemblies.

According to a preferred embodiment of the invention, the protective cap 140 is instead arranged between the first mask 120 and the second mask 130 and is integral with the second mask 130, thus reducing the number of parts of the indicator assembly 100 to be mounted. When mounting the indicator assembly 100 this configuration of the protective cap 140 also provides a wider gripping surface for the maneuvering of the second mask 130, which facilitates its positioning with respect to the first mask 120.

The protective cap 140 is provided with a flange 141 which replaces the flange (not shown) of the second mask 130 and performs the same function.

According to this configuration of the indicator assembly 100, once established the relative position between the first mask 120 and the second mask 130, tightening of the fixing screws of the first mask 120 causes its flange 123 to press the flange 141 of the protective cap 140 and to block it in position by friction together with the second mask 130.

In order to make the clamping action more effective and safer, a circumferential seat 142 may be formed on the side of the flange 141 of the protective cap 140 intended to face and contact the container C of the limit switch box. A gasket 143 such as an O-ring can be fitted in the circumferential seat 142 and pressed by the flange 123 of the first mask 120 against the container C thus contributing to frictional locking.

The present invention has hereto been disclosed with reference to preferred embodiments. It will be appreciated that there may be further embodiments based on the same inventive idea, as defined by the scope of protection of the claims set out below.

The invention claimed is:

1. A visual position indicator assembly for limit switch boxes, said indicator assembly comprising:
  i) an indicator element configured to be fitted in a shaft of a driving assembly of a limit switch box, the surface of said indicator element having a plurality of adjacent sectors alternately featuring a first color and a second color that are different from each other and/or alternately featuring different writings, said colors and/or writings indicating an operating condition of a device connectable to said limit switch box;
  ii) a first cap-shaped mask, said first mask comprising a plurality of through apertures formed in its mantle and on its top, wherein the size and the angular width of said through apertures substantially correspond to the size and angular width of said adjacent sectors the indicator element; and
  iii) a second mask, said second mask being coaxially fitted to the first mask and having the shape of a cap, the second mask comprising a plurality of through apertures formed in its mantle and on its top, said apertures having a size and angular width substantially corresponding to those of the through apertures formed in the first mask,
wherein the second mask is rotatable relative to the first mask.

2. The visual position indicator assembly according to claim 1, wherein the first mask is configured to be mounted on a container (C) of a limit switch box inside which a driving assembly is housed.

3. The visual position indicator assembly according to claim 2, wherein the first mask comprises a flange provided with a plurality of mounting holes.

4. The visual position indicator assembly according to claim 1, further comprising a protective cap made of a transparent material.

5. The visual position indicator assembly according to claim 4, wherein said protective cap is coaxially fitted between the first mask and the second mask and is integral with the second mask.

6. The visual position indicator assembly according to claim 5, wherein said protective cap comprises a flange and a circumferential seat formed on a side of the flange intended to face a container (C) of a limit switch box, a gasket being housed in said circumferential seat.

7. A limit switch box comprising a visual position indicator assembly according to claim 1.

* * * * *